(12) United States Patent
Rudrappa et al.

(10) Patent No.: US 8,901,377 B2
(45) Date of Patent: Dec. 2, 2014

(54) METHOD OF SUNFLOWER REGENERATION AND TRANSFORMATION USING RADICLE FREE EMBRYONIC AXIS

(75) Inventors: Thimmaraju Rudrappa, Hyderabad (IN); Prakash V. Girhepuje, Secunderabad (IN)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/294,202

(22) Filed: Nov. 11, 2011

(65) Prior Publication Data

US 2012/0144519 A1 Jun. 7, 2012

Related U.S. Application Data

(60) Provisional application No. 61/488,424, filed on May 20, 2011.

(51) Int. Cl.
*A01H 5/10* (2006.01)
*A01H 1/02* (2006.01)

(52) U.S. Cl.
USPC ............................ 800/294; 800/322; 800/268

(58) Field of Classification Search
None
See application file for complete search history.

(56) References Cited

U.S. PATENT DOCUMENTS

| | | | |
|---|---|---|---|
| 5,017,491 | A | 5/1991 | Freyssinet et al. |
| 6,265,638 | B1 | 7/2001 | Bidney et al. |
| 6,998,516 | B2 | 2/2006 | Brar et al. |

OTHER PUBLICATIONS

Hewezi et al. (Plant Cell, Tissue and Organ Culture 73: 81-86, 2003).*
Kalra et al. (Journal of Plant Biochemistry and Biotechnology,(1998), vol. 7, p. 107-108.*
Lewi et al. (Methods in Molecular Biology, vol. 343: Agrobacterium Protocols, 2/e, vol. 1, pp. 291-291 (2006)).*
Schrammeijer et al. (Plant Cell Reports (1990) 9, pp. 55-60).*
N. Dağüstü et al., Screening for High Callus Induction and Agrobacterium-Mediated Transformation of Sunflower, Biotechnol. & Biotechnol. Eq, pp. 933-937, 2008, vol. 22.
Jerry M. Green et al., Response of 98140 Corn with gat4621 and hra Transgenes to Glyphosate and ALS-Inhibiting Herbicides, Weed Science, Mar.-Apr. 2009, pp. 142-148, vol. 57, No. 2.
Tarek Hewezi et al., Dehydrating Immature Embryo Split Apices and Rehydrating With *Agrobacterium tumefaciens9*: A New Method for Genetically Transforming Recalcitrant Sunflower, Plant Molecular Biology Reporter, Dec. 2002, pp. 335-345, vol. 20.
Nathalie Knittel et al., Transformation of sunflower (*Helianthus annuus* L.): a reliable protocol, Plant Cell Reports, 1994, pp. 81-86, vol. 14.
Jobeth Malone-Schoneberg et al., Stable transformation of sunflower using *Agrobacterium* and split embryonic axis explants, Plant Science, 1994, pp. 199-207, vol. 103.
Sh. Mohamed et al., Stable genetic transformation of high oleic *Helianthus annuus* L. genotypes with high efficiency, Plant Science, 20006, pp. 546-554, vol. 171.
Olivier Lucas et al., Production of stable transgenic sunflowers (*Helianthus annuus* L.) from wounded immature embryos by particle bombardment and co-cultivation with *Agrobacterium tumefaciens*, Molecular Breeding, 2000, pp. 479-487, vol. 6.
K. Sankara Rao et al., *Agrobacterium*-mediated Transformation of Sunflower (*Helianthus annuus* L.): A Simple Protocol, Annals of Botany, 1999, pp. 347-354, vol. 83.
Barbara Schrammeijer et al., Meristem transformation of sunflower via *Agrobacterium*, Plant Cell Reports, 1990, pp. 55-60, vol. 9.

* cited by examiner

*Primary Examiner* — David T Fox
*Assistant Examiner* — Jared Shapiro (57) ABSTRACT

The present invention relates to methods and compositions for efficient regeneration and transformation of sunflower plants. The invention discloses an efficient method for *Agrobacterium*-mediated transformation and regeneration of mature, fertile sunflower plants.

8 Claims, 2 Drawing Sheets

SEQUENCE LISTING

<160> NUMBER OF SEQ ID NOS: 5

<210> SEQ ID NO 1
<211> LENGTH: 11518
<212> TYPE: DNA
<213> ORGANISM: Artificial Sequence
<220> FEATURE:
<223> OTHER INFORMATION: Binary vector used for transformation

<400> SEQUENCE: 1
tggcatgccc gttccataca gaagctgggc gaacaaacga tgctcgcctt ccagaaaacc      60
gaggatgcga accacttcat ccggggtcag caccaccggc aagcgccgcg acggccgagg     120
tcttccgatc tcctgaagcc agggcagatc cgtgcacagc accttgccgt agaagaacag     180
caaggccgcc aatgcctgac gatgcgtgga gaccgaaacc ttgcgctcgt tcgccagcca     240
ggacagaaat gcctcgactt cgctgctgcc caaggttgcc gggtgacgca caccgtggaa     300
acggatgaag gcacgaaccc agtggacata agcctgttcg gttcgtaagc tgtaatgcaa     360
gtagcgtatg cgctcacgca actggtccag aaccttgacc gaacgcagcg gtggtaacgg     420

```
cgcagtggcg gttttcatgg cttgttatga ctgtttttt  ggggtacagt ctatgcctcg    480
ggcatccaag cagcaagcgc gttacgccgt gggtcgatgt tgatgttat  ggagcagcaa    540
cgatgttacg cagcagggca gtcgccctaa aacaaagtta acatcatga  gggaagcggt    600
gatcgccgaa gtatcgactc aactatcaga ggtagttggc gtcatcgagc gccatctcga    660
accgacgttg ctggccgtac atttgtacgg ctccgcagtg gatggcggcc tgaagccaca    720
cagtgatatt gatttgctgg ttacggtgac cgtaaggctt gatgaaacaa cgcggcgagc    780
tttgatcaac gacctttgg  aaacttcggc ttccctgga  gagagcgaga ttctccgcgc    840
tgtagaagtc accattgttg tgcacgacga catcattccg tggcgttatc cagctaagcg    900
cgaactgcaa tttggagaat ggcagcgcaa tgacattctt gcaggtatct tcgagccagc    960
cacgatcgac attgatctgg ctatcttgct gacaaaagca agagaacata gcgttgcctt   1020
ggtaggtcca gcggcggagg aactctttga tccggttcct gaacaggatc tatttgaggc   1080
gctaaatgaa accttaacgc tatggaactc gccgcccgac tgggctggcg atgagcgaaa   1140
tgtagtgctt acgttgtccc gcatttggta cagcgcagta accggcaaaa tcgcgccgaa   1200
ggatgtcgct gccgactggg caatggagcg cctgccggcc cagtatcagc ccgtcatact   1260
tgaagctaga caggcttatc ttggacaaga agaagatcgc ttggcctcgc gcgcagatca   1320
gttggaagaa tttgtccact acgtgaaagg cgagatcacc aaggtagtcg gcaaataatg   1380
tctaacaatt cgttcaagcc gacgccgctt cgcggcgcgg cttaactcaa gcgttagatg   1440
cactatacgt aaccaactag tgcgctcttc cgcttcctcg ctcactgact cgctgcgctc   1500
ggtcgttcgg ctgcggcgag cggtatcagc tcactcaaag gcggtaatac ggttatccac   1560
agaatcaggg gataacgcag gaaagaacat gtgagcaaaa ggccagcaaa aggccaggaa   1620
ccgtaaaaag gccgcgttgc tggcgttttt ccataggctc cgcccccctg acgagcatca   1680
caaaaatcga cgctcaagtc agaggtggcg aaacccgaca ggactataaa gataccaggc   1740
gtttccccct ggaagctccc tcgtgcgctc tcctgttccg accctgccgc ttaccggata   1800
cctgtccgcc tttctccctt cgggaagcgt ggcgctttct catagctcac gctgtaggta   1860
tctcagttcg gtgtaggtcg ttcgctccaa gctgggctgt gtgcacgaac cccccgttca   1920
gcccgaccgc tgcgccttat ccggtaacta tcgtcttgag tccaacccgg taagacacga   1980
cttatcgcca ctggcagcag ccactggtaa caggattagc agagcgaggt atgtaggcgg   2040
tgctacagag ttcttgaagt ggtggcctaa ctacggctac actagaagga cagtatttgg   2100
tatctgcgct ctgctgaagc cagttacctt cggaaaaaga gttggtagct cttgatccgg   2160
caaacaaacc accgctggta gcggtggttt ttttgtttgc aagcagcaga ttacgcgcag   2220
aaaaaaagga tctcaagaag atcctttgat cttttctacg gggtctgacg ctcagtggaa   2280
cgaaaactca cgttaaggga ttttggtcat gagattatca aaaggatctt cacctagat   2340
ccttttaaat taaaaatgaa gcgtaccgac gatcttgctg cgttcggata ttttcgtgga   2400
gttcccgcca cagacccgga ttgaaggcga gatccagcaa ctcgcgccag atcatcctgt   2460
gacggaactt tggcgcgtga tgactggcca ggacgtcggc cgaaagagcg acaagcagat   2520
cacgcttttc gacagcgtcg gatttgcgat cgaggatttt tcggcgctgc gctacgtccg   2580
cgaccgcgtt gagggatcaa gccacagcag cccactcgac cttctagccg acccagacga   2640
gccaagggat ctttttggaa tgctgctccg tcgtcaggct ttccgacgtt tgggtggttg   2700
aacagaagtc attatcgcac ggaatgccaa gcactcccga ggggaaccct gtggttggca   2760
```

```
tgcacataca aatggacgaa cggataaacc ttttcacgcc cttttaaata tccgattatt    2820
ctaataaacg ctcttttctc ttaggtttac ccgccaatat atcctgtcaa acactgatag    2880
tttaaactga aggcgggaaa cgacaatctg atcatgagcg gagaattaag ggagtcacgt    2940
tatgaccccc gccgatgacg cgggacaagc cgttttacgt ttggaactga cagaaccgca    3000
acgttgaagg agccactcag caagctggta cgattgtaat acgactcact atagggcgaa    3060
ttgagcgctg tttaaacgct cttcaactgg aagagcggtt accagagctg gtcacctttg    3120
tccaccaaga tggaactgcg gcctcgaagc ttagatcagg atattcttgt ttaagatgtt    3180
gaactctatg gaggtttgta tgaactgatg atctaggacc ggataagttc ccttcttcat    3240
agcgaactta ttcaaagaat gttttgtgta tcattcttgt tacattgtta ttaatgaaaa    3300
aatattattg gtcattggac tgaacacgag tgttaaatat ggaccaggcc ccaaataaga    3360
tccattgata tatgaattaa ataacaagaa taaatcgagt caccaaacca cttgcctttt    3420
ttaacgagac ttgttcacca acttgataca aagtcatta tcctatgcaa atcaataatc    3480
atacaaaaat atccaataac actaaaaaat taaaagaaat ggataatttc acaatatgtt    3540
atacgataaa gaagttactt ttccaagaaa ttcactgatt ttataagccc acttgcatta    3600
gataaatggc aaaaaaaac aaaaggaaa agaaataaag cacgaagaat tctagaaaat    3660
acgaaatacg cttcaatgca gtgggaccca cggttcaatt attgccaatt ttcagctcca    3720
ccgtatattt aaaaaataaa acgataatgc taaaaaaata taaatcgtaa cgatcgttaa    3780
atctcaacgg ctggatctta tgacgaccgt tagaaattgt ggttgtcgac gagtcagtaa    3840
taaacggcgt caaagtggtt gcagccggca cacgagtc gtgtttatca actcaaagca    3900
caaatacttt tcctcaacct aaaaataagg caattagcca aaacaacttt gcgtgtaaa    3960 caacgctcaa tacacgtgtc attttattat tagctattgc ttcaccgcct tagctttctc    4020
gtgacctagt cgtcctcgtc ttttcttctt cttctctat aaaacaatac ccaaagagct    4080
cttcttcttc acaattcaga tttcaatttc tcaaaatctt aaaaactttc tctcaattct    4140
ctctaccgtg atcaaggtaa atttctgtgt tccttattct ctcaaaatct tcgattttgt    4200
tttcgttcga tcccaatttc gtatatgttc tttggtttag attctgttaa tcttagatcg    4260
aagacgattt tctgggtttg atcgttagat atcatcttaa ttctcgatta gggtttcata    4320
gatatcatcc gatttgttca aataatttga gttttgtcga ataattactc ttcgatttgt    4380
gatttctatc tagatctggt gttagtttct agtttgtgcg atcgaatttg tcgattaatc    4440 tgagttttc tgattaacag cggccgggat ccacacgaca ccatggctat tgaggttaag    4500
cctatcaacg cagaggatac ctatgacctt aggcatagag tgctcagacc aaaccagcct    4560
atcgaagcct gcatgtttga gtctgacctt actaggagtg catttcacct tggtggattc    4620
tacggaggta aactgatttc cgtggcttca ttccaccaag ctgagcactc tgaacttcaa    4680
ggtaagaagc agtaccagct tagaggtgtg gctaccttgg aaggttatag agagcagaag    4740
gctggttcca gtctcgtgaa acacgctgaa gagattctca gaaagagagg tgctgacatg    4800
atctggtgta atgccaggac atctgcttca ggatactaca ggaagttggg attcagtgag    4860
caaggagagg tgttcgatac tcctccagtt ggacctcaca tcctgatgta taagaggatc    4920
acataactag ctagtcagtt aacctagact tgtccatctt ctggattggc caacttaatt    4980
aatgtatgaa ataaaaggat gcacacatag tgacatgcta atcactataa tgtgggcatc    5040
aaagttgtgt gttatgtgta attactagtt atctgaataa aagagaaaga gatcatccat    5100
atttcttatc ctaaatgaat gtcacgtgtc tttataattc tttgatgaac cagatgcatt    5160
```

```
tcattaacca aatccatata catataaata ttaatcatat ataattaata tcaattgggt    5220
tagcaaaaca aatctagtct aggtgtgttt tgcgaatgcg gccgccaccg cggtggagct    5280
cgaattcatt ccgattaatc gtggcctctt gctcttcagg atgaagagct atgtttaaac    5340
gtgcaagcgc tactagacaa ttcagtacat taaaaacgtc cgcaatgtgt tattaagttg    5400
tctaagcgtc aatttgttta caccacaata tatcctgcca ccagccagcc aacagctccc    5460
cgaccggcag ctcggcacaa aatcaccact cgatacaggc agcccatcag tccgggacgg    5520
cgtcagcggg agagccgttg taaggcggca gactttgctc atgttaccga tgctattcgg    5580
aagaacggca actaagctgc cgggtttgaa acacggatga tctcgcggag ggtagcatgt    5640
tgattgtaac gatgacagag cgttgctgcc tgtgatcaaa tatcatctcc ctcgcagaga    5700
tccgaattat cagccttctt attcatttct cgcttaaccg tgacaggctg tcgatcttga    5760
gaactatgcc gacataatag gaaatcgctg gataaagccg ctgaggaagc tgagtggcgc    5820
tatttcttta gaagtgaacg ttgacgatcg tcgggcccag gtagaatccg cctgagtcgc    5880
aagggtgact tcgcctatat tggacgacgg cgcgcagagg gcgacctctt tttgggttac    5940
gattgtagga ttatcactaa acaatacat gaacatattc aaatggcaat ctctctaagg    6000
cattggaaat aaatacaaat aacagttggg tggagttttt cgacctgagg gcgttaacct    6060
tctgttaacc taaaagctct tgcccaaaca gcagaatcgg cgctaattgc cagcggcgga    6120
acttttccag tttcgcgaaa aatatcgcca ctggcaagga atgggtttga gatggcgaag    6180
tctgtcctaa aagcagcgcc tgtagttgta gggttgacgg ccttgatgga gcgtcatgcc    6240
gatgccctct cgagccaact tcaagcacat catcttaagg ttttcccgcc gcattccgag    6300
aagggcattc gaacattcgg gccatcggag gcgtccaagc tgctcggcgt tggcgagtca    6360
tatttacggc agaccgcgtc tgagatgcca gagttgaatg ttagcatgag cccgggtggc    6420
aggcgaatgt tctcaattga agatatccat gtgattcgga agtatatgga tcaggtcggc    6480
cgcgggaacc ggcgctacct gccacatcgt cgaggcggcg agcagcttca ggttatctct    6540
gtgatgaatt tcaaaggtgg gtcgggtaag accaccaccg ccgcgcatct ggcgcagtac    6600
ctcgctatgc gcggatatcg agtcttggcc attgatctcg atcctcaagc gagccttttct   6660 gcactctttg ggagccaacc ggagacggac gttggcccga acgaaacgct ctacggcgct    6720
ataaggtatg atgatgagca ggtggcaatc gaacgagtcg tccgagggac ttacattccc    6780
gacctccacc tgattcctgg taaccttgag ctgatggagt ttgaacacga tacgccacgc    6840
gcgctgatga accgcaaaga gggcgacacg ctcttttatg gtcgcatcag ccaagtaatt    6900
gaagatatcg cggataacta tgacgtcgtg gtcatcgact gccctcccca gcttgggtat    6960
ctcacgctat ccgcattgac tgcggcgacg tccattcttg tcacggtcca tccgcagatg    7020
ctggatgtga tgtcgatgaa ccagtttctg gcaatgacat cgaaccttt gcgtgaaatc     7080 gagaatgctg gcgccaagtt caagtttaat tggatgcgct atctgataac ccgtttcgaa    7140
ccgagcgacg gaccacagaa ccaaatggta ggttatctgc ggtcgatttt tggcgaaaat    7200
gtcctcaatt ttccgatgct taaaaccacc gcggtttcgg acgctggcct gacaaaccag    7260
actctattcg aagtggagcg tggcctgttc acgcgctcga cctatgatcg agccttggag    7320
gcgatgaacg ccgtcaacga cgagatcgaa acactgatca aaaaagcatg gggtaggccc    7380
acatgagccg gaagcacatc cttggcgtct caactgacgc ccctgagacg tcgcccgccg    7440
acaataggac ggcaaagaac cgctccatgc cgctcctcgg cgtaacaagg aaggagcgcg    7500
```

```
atccggcaac gaagctcaca gcgaacattg gtaacgcact gcgagagcaa aacgatcgtc    7560
ttagccgtgc cgaagagatc gagcggcgtc tcgctgaagg tcaggcagtg atagagttgg    7620
atgcctcgtc aatagaaccg tctttcgtgc aggatcgtat gcgagggggac attgacgggc   7680 tccttacttc gatccgggaa caaggacagc aagtcccaat ccttgtgcga ccgcatccga    7740
gccagccggg ccgatatcag gttgccttcg gccaccgccg gctacgcgcc gtttcagaac    7800
tcggacttcc ggtcagagcg gtcgttcgcg aactgacgga cgagcaagtg gtcgtagcac    7860
agggtcagga aaacaatgag cgcgaagatc ttaccttcat cgaaaaggcg cgcttcgcac    7920
atcgcctgaa caggcagttt tctcgagaga ttgtcatcgc cgcgatgtcg atcgacaaga    7980
gcaatttgtc caagatgctt ctgctcgttg acgccctccc ctctgaactg accgatgcta    8040
ttggtgccgc tcctggtgtt ggacggccga gttggcaaca acttgccgag ctgattgaga    8100
aagtttcttc accggccgac gtggctaaat atgctatgtc ggaggaagtt caagcgctgc    8160
catcggcaga acgattcaag gcggtgatcg ctagtctgaa gcccagtcgg gttgcgcgtg    8220
gacttcccga ggtcatggcc accccagacg gcaccagaat tgcacaggtg acgcagagca    8280
aggccaaact ggaaatcacg attgacagga aggcgacgcc cgattttgcg accttcgtgc    8340
tcgatcatgt gccagcgctg tatcaagcgt accacgctga gaaccaacgg aaacggggag    8400
agtaaaccgc aaaagaaaag agccccctca acgtcgccgt cgcggaagcc cttctgtctc    8460
tctagcgcga acagaatcgc atttcctcga atcctcgtca agagttttta gcgccgtttt    8520
ggtgagctga tttcctttgc ctgctgaaag gtgaaagatg atgcagacag gaagtgtaac    8580
gacgccattc gggcggcggc caatgacgct tgcgcttgtg cggcgccaga cggcgctggc    8640
cgatatcaaa caaggcaaga cagcggacaa gtggaaggtc tttagagacg cgtccgcggc    8700
tatgaaacta cttggaatcc agtccaacag tcttgccgtc cttgatgcgc tattgagctt    8760
tcacccggaa acggagttgc gtcaggaggc acagctgatc gtcttcccgt cgaatgctca    8820
gcttgccctt cgggcgcatg ggatggctgg cgcgactttg cgtaggcaca tcgccatgct    8880
cgtggagtca ggcttgatcg tccggaagga tagcgccaac ggaaagcgtt acgctcgtaa    8940
ggatggcgct ggtcagatcg agcgcgcgtt tggcttcgat ttgtctccgc ttctcgcgcg    9000
gtccgaagag ctagcgatga tggcacagca ggtgatggcc gatcgagcag cattcaggat    9060
ggccaaagaa agtctgacga tttgccgacg ggacgttcgg aagctaatta cggcagctat    9120
ggaagaggga gcggagggcg actggcaagc tgtcgaggaa gtctatgtgg aacttgtggg    9180
tagaattcca cgcgccccga cgcttgctga tgtagagtca attctcgaag agatgtggat    9240
gctccaggaa gagataatca accggttgga aattagagac aattcagaaa ataatagcac    9300
caatgctgcc cagagcgagc agcacataca gaattcaaaa cccgaatccg ttaatgaact    9360
tgaacctcgc tctgaaaagg agcagggcgc taagccgagt gaaatagacc gggcaaggag    9420
cgagccgata aaagcgttcc ccctcgggat gatcctgaaa gcatgcccga ccattggcaa    9480
ttatgggccg agcggtgcgg ttgctagctg gcgtgacctc atgtcggctg cggtggtggt    9540
tcggtctatg ctgggggtca gcccgtcggc ttaccaagac gcgtgtgagg caatgggacc    9600
ggagaatgcg gcagcagcga tggcgtgcat tttggagcga gcgaacttca tcaattcgcc    9660 cggggggctat ctccgagatc tgacacggcg gagcgagctt gggaagtttt cacttggccc    9720
gatgataatg gcgctcttga aggctagcgg gcagggggacg ttgcggtttg gctagaatta    9780
gcgagtatgg agcaggatgg tctgtggtca gctgaccaca gacctaatag gttgaaaaca    9840
tgagcgtttt ttggatgatc gacagaccat ccgattcccg gagtaccaag cgtgctctga    9900
```

```
tgggagcgat aacattactc aacaagcacg aaggccccat gccgatcgtt gatcgtgaag    9960
gagagcctgc tctacatgcg gcggtatttt gccggccgag gcatgtagtc gcggagcact   10020
gcctatttac tgccctaggc acaaacgttg actcttggat cgagctggca gacaaagcaa   10080
taacccacac agaggacgat taatggctga cgaagagatc cagaatccgc cggacggtac   10140
tgctgctgcc gaagttgagc cggctgctcc tagaggtaga agagcaaaga aagcaccagc   10200
cgaaacagcc cgcacgggat cgttcaaatc cgtgaagccg aaaacccgcg gcctcagcaa   10260
ccgagaaaaa ctggagaaga tcggtcaaat cgaagctcag gtcgctggcg gcgcaacctt   10320
gaaggacgcc gttaagatcg tgggtatttc cgttcagacc tattatcaat ggaagagagc   10380
tgcggttcaa cctgtctcac agaatccggc cgtgtctgtt tcagttgacg atgaactcgg   10440
cgagttcatc caactcgagg aggaaaatat gcagtagctg taacctcgaa gcgtttcact   10500
tgtaacaacg attgagaact tttgtcataa aattgaaata cttggttcgc attttcgtca   10560
tccgcggtca gccgcaattc tgacgaactg cccatttagc tggagatgat tgtacatcct   10620
tcacgtgaaa atttctcaag cgctgtgaac aagggttcag attttagatt gaaaggtgag   10680
ccgttgaaac acgttcttct tatcgatgac gatgtcgcta tgcggcatct tattatcgaa   10740
taccttacga tccacgcctt caaagtgacc gcggtagccg acagcaccca gttcactaga   10800
gtactctctt ccgcgacggt cgatgtcgtg gttgttgatc taaatttagg tcgtgaagat   10860
gggcttgaga tcgttcgaaa tctggcggca aagtctgata ttccaatcat aattatcagt   10920
ggcgaccgcc ttgaggagac ggataaagtt gttgcactcg agctaggagc aagtgatttt   10980
atcgctaagc cgtttagtac gagagagttt cttgcacgca ttcgggttgc cttgcgcgtg   11040
cgccccaacg ttgtccgctc caaagaccga cggtcttttt gttttactga ctggacactt   11100
aatctcaggc aacgtcgctt gatgtccgaa gctggcggtg aggtgaaact tacggcaggt   11160
gagttcaatc ttctcctcgc gttttttagag aaaccccgcg acgttctatc gcgcgagcaa   11220
cttctcattg ccagtcgagt acgcgacgag gaggtttacg acaggagtat agatgttctc   11280
attttgcggc tgcgccgcaa acttgaggca gatccgtcaa gccctcaact gataaaaaca   11340
gcaagaggtg ccggttattt cttttgacgcg gacgtgcagg tttcgcacgg ggggacgatg   11400
gcagcctgag ccaattgcat ttggctctta attatctggc tcaaaaggtg actgaggacg   11460
cggccagcgg cctcaaacct acactcaata tttggtgagg ggttccgata ggtctgca    11518
```

<210> SEQ ID NO 2
<211> LENGTH: 20
<212> TYPE: DNA
<213> ORGANISM: Artificial Sequence
<220> FEATURE:
<223> OTHER INFORMATION: Forward primer-1

<400> SEQUENCE: 2
ttcagctcca ccgtatattt                                                   20

<210> SEQ ID NO 3
<211> LENGTH: 20
<212> TYPE: DNA
<213> ORGANISM: Artificial Sequence
<220> FEATURE:
<223> OTHER INFORMATION: reverse primer-1

<400> SEQUENCE: 3
gaatctcttc agcgtgtttc                                                   20

```
<210> SEQ ID NO 4
<211> LENGTH: 20
<212> TYPE: DNA
<213> ORGANISM: Artificial Sequence
<220> FEATURE:
<223> OTHER INFORMATION: forward primer-2

<400> SEQUENCE: 4
cgtgtaaaca acgctcaata                                             20

<210> SEQ ID NO 5
<211> LENGTH: 20
<212> TYPE: DNA
<213> ORGANISM: Artificial Sequence
<220> FEATURE:
<223> OTHER INFORMATION: reverse primer-2

<400> SEQUENCE: 5
cacaactttg atgcccacat                                             20
```

METHOD OF SUNFLOWER REGENERATION AND TRANSFORMATION USING RADICLE FREE EMBRYONIC AXIS

CROSS REFERENCE TO RELATED APPLICATIONS

This application claims the benefit of India Provisional Application No. 2883/DEL/2010, filed Dec. 3, 2010, and U.S. Provisional Application No. 61/488,424, filed May 20, 2011; the entire content of each is herein incorporated by reference.

FIELD OF THE INVENTION

This method pertains to the methods and compositions for efficient regeneration and transformation of sunflower plants.

BACKGROUND OF THE INVENTION

The sunflower (*Helianthus annus* L.) is one of the most important oil seed crops in the world. Conventional sunflower breeding programs aim at obtaining sunflower cultivars having improved agronomic characteristics such as increased oil and nutritional content, disease resistance and oil quality. To be able to broaden the genetic variation of cultivated sunflower, optimization of tissue culture and transformation techniques is necessary. However, sunflower is known as one of the most recalcitrant species for tissue culture and genetic transformation. Progress in sunflower transformation has been restricted by the limitations of available regeneration systems and problems combining regeneration and transformation within the same cells. Reliable and reproducible transformation methods rely on high transformation rates, efficient regeneration procedures, and available performing selection systems to discriminate and develop dedifferentiated transformed cells (Dağüstü, N. et al. (2008) *Biotechnol. & Biotechnol Eq.* 22: 933-937; Mohamed, Sh. et. al. (2006) *Plant Sci.* 171: 546-554; Hewezi, T. et al (2002) *Plant Mol. Biol. Rep.* 20: 335-345).

The protocols currently available for transformation of sunflower plants involve regeneration of plants from transformed explants from mature or immature embryos, or from embryonic parts such as embryonic axes, hypocotyls or cotyledons (U.S. Pat. No. 6,998,516), or depend on regeneration of mature and fertile plants from somatic embryos (U.S. Pat. No. 5,017,491). Also, many of these transformation protocols require extensive preparation of the explants for transformation, or extensive equipment such as that involving particle bombardment of the explants (Malone-Schoneberg, J. et al (1994) *Plant Sci.* 103: 199-207; U.S. Pat. No. 6,265,638; Knittel, N. et al. (1994) *Plant Cell Rep.* 14: 81-86, Lucas, O. et al (2000) *Mol. Breeding* 6: 479-487), have low transformation efficiencies (Schrammeijer, B. et al. (1990) *Plant Cell Rep.* 9:55-60), involve grafting of transformed shoots onto non-transgenic rootstocks to recover transgenic seeds, result in recovery of chimeric plants (Rao, K. S. (1999) *Annals Bot.* 83:347-354) or exhibit low regeneration efficiencies of fertile transgenic sunflower plants from the transformed explants.

Methods and compositions for *Agrobacterium*-mediated high-efficiency transformation and efficient, reproducible regeneration of mature, fertile transgenic sunflower plants are required, and are disclosed herein.

SUMMARY OF THE INVENTION

The present invention provides methods for efficient transformation and regeneration of mature and fertile transgenic sunflower plants. The invention also encompasses methods for efficient regeneration of non-transformed mature and fertile sunflower plants.

In one embodiment, low light intensity is used for the steps of shoot or root regeneration, or both, from a transformed or an untransformed explant.

One embodiment of the present invention concerns a method for producing a transformed sunflower plant wherein the transformed sunflower plant comprises in its genome at least one heterologous nucleic acid of interest. The method comprises the steps of obtaining a radicle-free mature embryonic axis explant from a non-germinated sunflower seed, transforming the radicle-free mature embryonic axis explant with *Agrobacterium*, wherein the *Agrobacterium* contains at least one recombinant construct comprising at least one heterologous nucleic acid of interest; followed by regenerating a shoot from the transformed explant by culturing the explant under cycles of a first light and a first dark period wherein the first light period has a first light intensity in the range of 10-60 $\mu E\ m^{-2}\ S^{-1}$; and as a preferred embodiment, the first light intensity in the first light period may further be in the range of 10-50 $\mu E\ m^{-2}\ S^{-1}$; shoot regeneration is followed by inducing rooting by culturing the regenerated shoot in a media wherein the media comprises an auxin, wherein the culturing is performed under cycles of a second light and a second dark period and the second light period has a second light intensity in the range of 10-60 $\mu E\ m^{-2}\ S^{-1}$; and as a preferred embodiment, the second light intensity in the second light period may further be in the range of 10-50 $\mu E\ m^{-2}\ S^{-1}$.

In an embodiment of the present invention, the *Agrobacterium* used for transformation may be *Agrobacterium tumefaciens*.

An additional embodiment of this invention is the above method when the transformed sunflower plant is produced with transformation efficiency greater than 1.0%.

Another embodiment of the present invention concerns a method for producing a mature and fertile sunflower plant from a radicle-free mature embryonic axis explant, the method for producing a mature and fertile sunflower comprises the steps of obtaining a radicle-free mature embryonic axis explant from a non-germinated sunflower seed; regenerating a shoot from the transformed explant by culturing the explant under cycles of a first light and a first dark period wherein the first light period has a first light intensity in the range of 10-60 $\mu E\ m^{-2}\ S^{-1}$; as a preferred embodiment, the first light intensity in the first light period may further be in the range of 10-50 $\mu E\ m^{-2}\ S^{-1}$; shoot regeneration is followed by the step of inducing rooting by culturing the regenerated shoot in a media wherein the media comprises an auxin, and the culturing is performed under cycles of a second light and a second dark period and the second light period has a second light intensity in the range of 10-60 $\mu E\ m^{-2}\ S^{-1}$; as a preferred embodiment, the second light intensity in the second light period may further be in the range of 10-50 $\mu E\ m^{-2}\ S^{-1}$.

As a preferred embodiment, the auxin in the rooting media may be indole-acetic acid (IAA), and in one embodiment, the concentration of indole-acetic acid can be in the range of 0.1-1.0 mg/l.

In another embodiment, the invention includes transformed sunflower plant cells, tissues, plants, and seeds. The invention encompasses regenerated, mature and fertile transgenic sunflower plants, transgenic seeds produced therefrom, T1 and subsequent generations. The transgenic sunflower plant cells, tissues, plants, and seeds may comprise at least one recombinant DNA construct of interest. The invention also encompasses mature and fertile non-transformed sunflower plants regenerated by the methods and compositions of the present invention, and their progeny seeds, and subsequent generations.

BRIEF DESCRIPTION OF THE DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO: 1 is the sequence of the binary vector, PHP43534, used for sunflower transformation.

SEQ ID NO: 2 is the sequence of the forward primer from primer set 1 used for PCR analysis to test the transformed sunflower plants for presence of the transgene.

SEQ ID NO: 3 is the sequence of the reverse primer from primer set 1 used for PCR analysis to test the transformed sunflower plants for presence of the transgene.

SEQ ID NO: 4 is the sequence of the forward primer from primer set 2 used for PCR analysis to test the transformed sunflower plants for presence of the transgene.

SEQ ID NO: 5 is the sequence of the reverse primer from primer set 2 used for PCR analysis to test the transformed sunflower plants for presence of the transgene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein.

The terms "dicot" and "dicotyledonous plant" are used interchangeably herein.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

A recombinant DNA construct (including a suppression DNA construct) of the present invention may comprise at least one regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

A number of promoters can be used in recombinant DNA constructs of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in Arabidopsis (Kasuga et al. (1999) Nature Biotechnol. 17:287-91).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters may be derived in their entirety from a native gene, or be composed of different elements derived from different promoters found in nature, or even comprise synthetic DNA segments.

In another embodiment of the present invention, a recombinant DNA construct of the present invention further comprises an enhancer or silencer.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The terms "entry clone" and "entry vector" are used interchangeably herein.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

As will be evident to one of skill in the art, any nucleic acid of interest can be used in the methods of the present invention. Any recombinant construct comprising a nucleic acid of interest that may be introduced into a plant cell may be employed in the methods of the present invention. A sunflower plant can be engineered to express genes conferring different phenotypes, examples of such genes include, but are not limited to, disease and insect resistance genes, genes conferring nutritional value, genes to confer male and/or female sterility, antifungal, antibacterial or antiviral genes, and the like. Likewise, the method can be used to transfer any nucleic acid to control gene expression. Examples of nucleic acids that could be used to control gene expression include, but are not limited to, antisense oligonucleotides, suppression DNA constructs, or nucleic acids encoding transcription factors.

Genes of interest can be genes conferring modified agronomic traits and characteristics including, but not limited to, yield and heterosis increase, increased oil and nutritional value. General categories of genes of interest include, for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics and commercial products.

Agronomically important traits such as oil, starch and protein content can be genetically altered in addition to using traditional breeding methods. Modifications include increasing content of oleic acid, saturated and unsaturated oils, increasing levels of lysine and sulfur and providing essential amino acids, and also modification of starch. Other proteins include methionine-rich plant proteins such as from sunflower seed (Lilley, et al. *Proceedings of the World Congress on Vegetable Protein Utilization in Human Foods and Animal Feedstuffs*, Applewhite, H. (ed.); American Oil Chemists Soc., Champaign, Ill.; (1989) 497-502; corn (Pedersen, et al. *J. Biol. Chem*. (1986) 261:6279; Kirihara et al. *Gene* (1988) 71:359; and rice (Musumura, et al. *Plant Mol. Biol.* (1989) 12:123. These references are herein incorporated by reference.

In addition to the various regulatory elements, the recombinant vector can also contain a selectable or a screenable marker, or both. The nucleic acid sequence serving as the selectable or a screenable marker functions to produce a phenotype in cells that facilitates their identification relative to cells not containing the marker. Useful selectable and screenable markers include, but are not limited to, GUS, green fluorescent protein (GFP), luciferase (LUX), antibiotic resistance sequences, and herbicide tolerance sequences.

Selectable marker genes may be utilized for the selection of transformed cells or tissues. Examples of selectable marker genes include, but are not limited to, genes encoding antibiotic resistance, such as nptII which encodes neomycin phosphotransferase II (NEO), hpt which encodes hygromycin phosphotransferase (HPT), and the monocot-optimized cyanamide hydratase gene (moCAH) (see U.S. Pat. No. 6,096,947) as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech*. 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol*. 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol*. 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res*. 19:46474653; Hillenand-Wissman (1989) *Topics Mol. Struc.*

Biol. 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Where appropriate, the gene sequence(s) may be modified to optimize for increased expression in the transformed plant. Examples of such modifications include, but are not limited to, synthesizing the genes using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391 and Murray et al. (1989) *Nucleic Acids Res.* 17:477-498.

Additional sequence modifications are known to enhance gene expression in a cellular host. Examples of such modifications include, but are not limited to, elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The nucleotide constructs of the invention may be comprised of expression cassettes for expression in sunflower plants. The expression cassette will include one or more than one regulatory sequence operably linked to a nucleic acid sequence of interest.

*Agrobacterium*-mediated gene transfer exploits the natural ability of *Agrobacterium tumefaciens* and *A. rhizogenes* to transfer DNA into plant chromosomes. *Agrobacterium* is a plant pathogen that transfers a set of genes encoded in a region called T-DNA of its tumor-inducing (Ti) plasmid or hairy-root-inducing (Ri) plasmid into plant cells at wound sites. This process depends on the cis acting T-DNA border sequences that flank the transferred DNA and the trans acting virulence (vir) functions encoded by the Ti plasmid or Ri plasmid and the bacteria's chromosome. The typical result of gene transfer in *A. tumefaciens* is a tumorous growth called a crown gall. The result of gene transfer in *A. rhizogenes* is hairy root disease. In both cases, gene transfer results in stable integration of the T-DNA region into a plant host chromosome. The ability to cause crown gall disease or hairy root disease can be removed by deletion of the oncogenic genes in the T-DNA without loss of DNA transfer and integration. When the oncogenic genes are removed in this manner, the *Agrobacterium* is said to be disarmed or nononcogenic.

Such *Agrobacterium*-mediated gene transfer systems are modified to contain a heterologous or foreign nucleotide sequence of interest, such as a foreign gene or genes of interest, to be expressed in the transformed plant cells. The heterologous nucleotide sequence to be transferred is incorporated into the T-DNA region, which is flanked by imperfect 25-bp terminal repeats or T-DNA border sequences that define the end points of an integrated T-DNA. Any sequences between these terminal repeats become integrated into the plant nuclear DNA (Fraley et al. (1983) *Proc. Natl. Acad. Sci. USA* 80:4803; Watson et al. (1985) *EMBO J.* 4:277; Horsch et al. (1985) *Science* 227:1229; Hernalsteens et al. (1984) *EMBO J.* 3:3039; Comai et al. (1984) *Nature* 317:741; Petit et al. (1986) *Mol. Gen. Genet.* 202:388-393; Shah et al. (1986) *Science* 233:478; Bytebier et al. (1987) *Proc. Natl. Acad. Sci. USA* 84:5345; Schafew et al. (1987) *Nature* 327:529; McKnight et al. (1987) *Plant Mol. Biol.* 8:439-445; Potrykus (1990) *Biotechnol* 8:535; Grimsley et al. (1987) *Nature* 325:177; Gould et al. (1991) *Plant Physiol.* 95:426; Ishida et al. (1996) *Nature Biotechnology* 14:745; and U.S. Pat. No. 5,591,616, and the references cited therein).

Embryogenesis in higher plants describes the period of post-fertilization development of the zygote, during which the zygote undergoes a complex series of morphological and cellular changes resulting in the formation of a developmentally arrested "mature embryo" comprised of an embryonic axis with shoot and root poles and cotyledon(s), which often contains high levels of storage macromolecules such as proteins and lipids. During the final stages of embryogenesis, embryos also acquire the ability to withstand desiccation and eventually enter a period of metabolic quiescence (Kermode, 1990). The mature embryo remains dormant until it encounters conditions appropriate for germination.

Sunflower embryos undergo distinct changes during maturation. In a first stage (about 1-3 weeks after fertilization), the entire embryo is transparent, semi-solid and very small. As the embryo increases in size, the outermost epidermal layers take on a beige color while the inner cotyledonary tissue remains transparent and semi-solid; this stage extends from about 3-4 weeks after pollination. In the third stage of immature embryos, the embryos reach maximum size, are beige-brown throughout and solid and the cotyledons are fully formed. This stage extends from about 4-8 weeks after pollination. When seeds are mature (about 5-10 weeks after pollination), the seeds cease drawing moisture from the parent, the embryos and pericarps become smaller, darker in color and denser as the moisture content of the seed decreases. The maturation time for seeds can vary considerably with sunflower genotype and growing conditions, however the physical changes associated with the stages are conserved (U.S. Pat. No. 5,030,572, West, M. A. L. et al (1993) *Plant Cell* 5:1361-1369).

A mature plant embryo contains two specialized organ systems: the "embryonic axis" and "cotyledons" (Yadegiri et al (1994) *Plant Cell* 6: 1713-1729).

The "embryonic axis" consists of the epicotyl, hypocotyl and radicle regions and contains the shoot and root meristems that are responsible for differentiating organ systems of the postembryonic plant.

In the "mature embryonic axis", a shoot (or the epicotyl), the cotyledon(s), hypocotyl, and radicle are distinguishable.

The "epicotyl" is the portion of embryonic axis above attachment of cotyledons, and is the primary shoot tip.

The "hypocotyl" is the part of embryonic axis below attachment of cotyledons and above the radicle. Upon germination, the hypocotyl pushes the cotyledons above the ground to develop. It eventually becomes part of the plant stem.

The "radicle" is the embryonic root of the plant, and is terminal part of embryonic axis. It grows downward in the soil, and is the first part of a seedling to emerge from the seed during the process of germination.

The "cotyledon" is a terminally differentiated structure that functions in the accumulation of storage reserves that are consumed by the germinating seedling after seed dormancy ends.

"Germination" is the process by which a zygotic embryo develops into a seedling. Germination is initiated by imbibition or fluid uptake and the embryo tissue starts swelling. The embryo then proceeds through various biophysical, biochemical and morphological events which result in visible development of the embryo along its axis.

Usually germination is complete when a part of the embryo, usually the radicle, extends to penetrate the structures that surround it (Bewley, J. D. (1997) Plant Cell 9:1055-1066).

For purposes of this invention, "non-germinated seed" is a mature seed that does not show any visible signs of germination. The term non-germinated embryo as used herein includes germinating embryos which display swelling but no visible signs of embryo development.

"Controlled light conditions" refers to conditions wherein the intensity and duration of light exposure are controlled.

"Dark or limited lighting conditions" refers to visible light having a maximum intensity from about $0\mu$ Einsteins $m^{-2}$ $sec^{-1}$ to about $5\mu$ Einsteins $m^{-2}$ $sec^{-1}$ ($\mu Em^{-2} s^{-1}$).

"Low light intensity" refers herein to visible light having a maximum intensity of about 60 $\mu Em^{-2} s^{-1}$.

"Medium light intensity" refers herein to visible light ranging from 60 $\mu Em^{-2} s^{-1}$ to 100 $\mu Em^{-2} s^{-1}$.

"High light intensity" refers herein to visible light having a minimum intensity of 100 $\mu Em^{-2} s^{-1}$.

"Regeneration," as used herein, refers to a morphogenetic response that results in the production of new tissues, embryos, organs, whole plants or fragments of whole plants that are derived from a single cell, or a group of cells. In the present invention, the term "regeneration" encompasses production of new tissues, organs, whole plants or fragments of whole plants that are derived from a single cell, or a group of cells. Regeneration may proceed indirectly via somatic embryogenesis or directly without an intervening somatic embryo formation phase.

"Regenerative capacity" refers to the ability of a plant cell to undergo regeneration.

The term "explant" as used herein refers to plant cells, tissues, or organs that are separated from the whole plant or seed. These plant cells, tissues or organs may be cultured in vitro for the purpose of initiating a plant cell culture or a plant tissue culture. For example, an explant may be the cotyledons alone containing the proximal end to the seedling that may contain cells capable of generating roots upon transformation; or an explant may be a portion of the embryonic axis above and including, the hypocotyl that may contain cells capable of generating whole plants.

The term "meristem" or "meristematic cells" or "meristematic tissue" can be used interchangeably and is intended to mean undifferentiated plant tissue, which continually divides, forming new cells, as that found at the tip of a stem or root.

The term "transformation efficiency" as used herein can be measured by the number of transformed shoots recovered out of total number of explants co-cultivated, i.e., (No. of PCR positive transgenic shoots/Total No. of explants co-cultivated)×(100%).

Auxins are a class of naturally occurring or synthetic organic (carbon-containing) plant hormones that increase, in low concentrations, the rate of cell elongation in stems, and have the capacity to stimulate cell division in excised plant tissues, among other influences. In addition to their role in cell division and cell elongation, auxins influence other developmental processes, including root initiation. Examples of auxin and auxin-type growth regulators that can be used for the methods and compositions of the current invention include, but are not limited to, indole-acetic acid (IAA), 3-indolebutyric acid (IBA), α-napthaleneacetic acid (NAA), 2,4-dichlorophenoxyacetic acid (2,4-D), 4-(2,4-dichlorophenoxy)butyric acid, 2,4,5-trichlorophenoxyacetic acid (2,4,5-T), 3-amino-2,5-dichlorobenzoic acid (chloramben), (4-chloro-2-methylphenoxy)acetic acid (MCPA), 4-(4-chloro-2-methylphenoxy)butanoic acid (MCPB), mecoprop, diclopop, quinclorac, picloram, triclopyr, clopyralid, fluroxypyr or dicamba.

The present invention describes methods and compositions for transformation and regeneration, or just regeneration, of a mature and fertile sunflower plant. In another embodiment, the invention describes methods comprising steps wherein controlled light conditions are used for the steps of shoot or root regeneration, or both, from a transformed or a non-transformed explant. In an embodiment, low or medium light intensity can be used for the steps of shoot or root regeneration, or both, from a transformed or a non-transformed explant. In another embodiment, low light intensity can be used for the steps of shoot or root regeneration, or both, from a transformed or an untransformed explant.

In an embodiment, the invention describes a method and compositions for regeneration of a transformed or non-transformed mature and fertile sunflower plant from an explant without an intervening somatic embryogenesis step.

Embodiments of the present invention include the following:

In one embodiment, the present invention concerns a method for producing a transformed sunflower plant wherein the transformed sunflower plant comprises in its genome at least one recombinant DNA construct of interest. The method comprises the steps of obtaining a radicle-free mature embryonic axis explant from a non-germinated sunflower seed, transforming the radicle-free mature embryonic axis explant with *Agrobacterium*, wherein the *Agrobacterium* contains at least one recombinant construct comprising at least one nucleic acid of interest; followed by regenerating a shoot from the transformed explant by culturing the explant under cycles of a first light and a first dark period wherein the first light period has a first light intensity in the range of 10-60 μE $m^{-2} s^{-1}$; and in an embodiment, the first light intensity in the first light period may further be in the range of 10-50 μE $m^{-2} S^{-1}$; shoot regeneration is followed by inducing rooting by culturing the regenerated shoot in a media wherein the media comprises an auxin, wherein the culturing is performed under cycles of a second light and a second dark period and the second light period has a second light intensity in the range of 10-60 μE $m^{-2} S^{-1}$; and in an embodiment, the second light intensity in the second light period may further be in the range of 10-50 μE $m^{-2} s^{-1}$.

In another embodiment, the *Agrobacterium* used for transformation may be *Agrobacterium tumefaciens*.

An additional embodiment of this invention is the above method when the transformed sunflower plant is produced with transformation efficiency greater than 1.0%, greater than 1.5%, greater than 2.0%, greater than 2.5%, greater than 3.0%, greater than 3.5% or greater than 4.0%.

Another embodiment of the present invention concerns a method for producing a mature and fertile sunflower plant from a radicle-free mature embryonic axis explant, the method for producing a mature and fertile sunflower comprises the steps of obtaining a radicle-free mature embryonic axis explant from a non-germinated sunflower seed; regenerating a shoot from the transformed explant by culturing the explant under cycles of a first light and a first dark period wherein the first light period has a first light intensity in the range of 10-60 μE $m^{-2} s^{-1}$; in one embodiment, the first light intensity in the first light period may further be in the range of 10-50 μE $m^{-2} s^{-1}$; shoot regeneration is followed by the step of inducing rooting by culturing the regenerated shoot in a media wherein the media comprises an auxin, and the culturing is performed under cycles of a second light and a second dark period and the second light period has a second light intensity in the range of 10-60 µE m$^{-2}$ s$^{-1}$; in one embodiment, the second light intensity in the second light period may further be in the range of 10-50 µE m$^{-2}$ s$^{-1}$. In another embodiment, the present invention includes transformed sunflower plant cells, tissues, plants, and seeds. The invention encompasses regenerated, mature and fertile transgenic sunflower plants, transgenic seeds produced therefrom, T1 and subsequent generations. The transgenic sunflower plant cells, tissues, plants, and seeds may comprise at least one recombinant DNA construct of interest. The invention also encompasses mature and fertile sunflower plants regenerated by the methods and compositions of the present invention, and their progeny seeds, and subsequent generations.

In an embodiment, the auxin concentration may be in the range of 0-3 mg/liter.

As an embodiment, the auxin may be IAA. As another embodiment, IAA concentration may be in the range of 0.1-1.0 mg/l. In one embodiment, the IAA concentration is 0.2 mg/l.

In another embodiment, the methods described herein may further comprise obtaining a progeny plant.

In another embodiment, the methods described herein may further comprise obtaining seed from the progeny plant.

In another embodiment, the progeny plants and seeds obtained by the methods described herein.

The method for sunflower transformation and regeneration described in the present invention can be used for transformation and regeneration of other dicots. In an embodiment, this method can be used in crop species. The crop species can be soybean & canola. This method can be used for transformation and regeneration of elite varieties of soybean and canola that are not usually used for transformation, or are recalcitrant to transformation.

EXAMPLES

Example 1

Construction of Binary Plasmids

Figure 1:
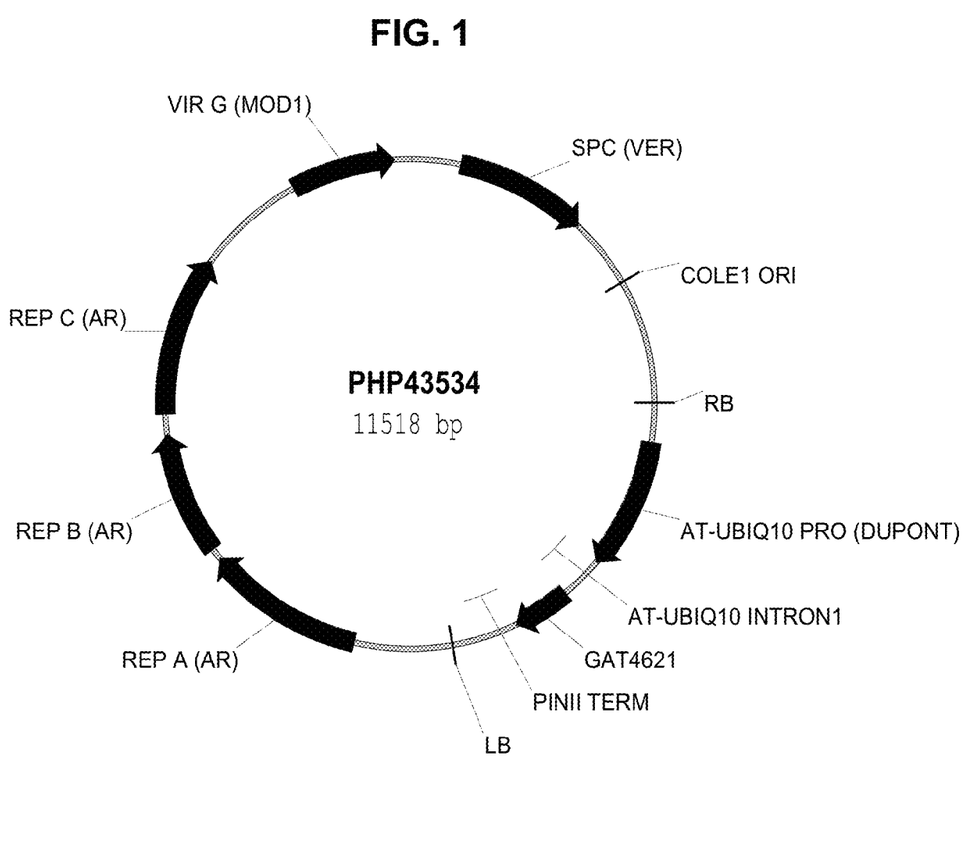
FIG. 1 is a schematic representation of the binary vector used for sunflower transformation.

Plasmid PHP43534 (FIG. 1; SEQ ID NO: 1) was constructed to test the transformation method and is an *Agrobacterium* binary plasmid that contains AT-UBIQ10 promoter driving the expression of GAT4621 (Green et al. (2009) *Weed Science* 57:142-148. 2009) and potato proteinase inhibitor II (PIN II) terminator region (An et al. (1989) *Plant Cell* 1:115-122) between the right and left T-DNA borders. PHP43534 also harbors bacterial spectinomycin resistance gene for bacterial selection. The GAT4621 which provides glyphosate resistance was used as plant selectable marker.

Example 2

*Agrobacterium* Transformation

*Agrobacterium tumefaciens* strain LBA4404pSB1 was transformed with the spectinomycin resistant binary vector, PHP43534 using the freeze-thaw method of Holsters et al. (1978) *Mol. Gen. Genetics* 1:181-187. Transformed, spectinomycin resistant-resistant, isolates were selected on solidified LB medium (Luria Bertani) with Rifampicin (10 mg/L), Tetracyclin (5 mg/L) and Spectinomycin (50 mg/L).

Single individual colonies were picked and inoculated in to liquid LB medium, grown to an $OD_{600}$ of 1.0, and used to make glycerol-based freezer stocks, which are stored at −80° C. These stocks can be used to reinitiate *Agrobacterium* cultures. Liquid, shaking cultures were initiated from glycerol stocks and used for binary plasmid isolation (QIAGEN Inc., Chatsworth, Calif.). Plasmid isolated from *Agrobacterium* was digested with restriction enzymes and compared to digested source plasmid preparations to verify that fragments were not altered in size due to the transformation procedure. The LBA4404pSB1/PHP43534 was used for sunflower transformation.

Example 3

Sunflower Transformation

Sunflower transformation protocol (FIG. 2) consisted of direct co-cultivation of embryonic axis explant with overnight grown *Agrobacterium* strain LBA4404pSB1/pPHP43534 described in Example 2. The detailed protocol followed is described below 1. Sunflower mature embryonic explants were isolated from dried mature seeds of sunflower are surface sterilized, imbibed with water overnight, by splitting open the seeds and carefully removing both the cotyledons and isolating the mature zygotic embryos. The isolated embryos were incubated in MS liquid medium containing MS basal salts (Phytotech)+MS vitamins (Phytotech labs)+3% Sucrose (i.e., 30 g/L) till the isolation is completed.

Figure 2:
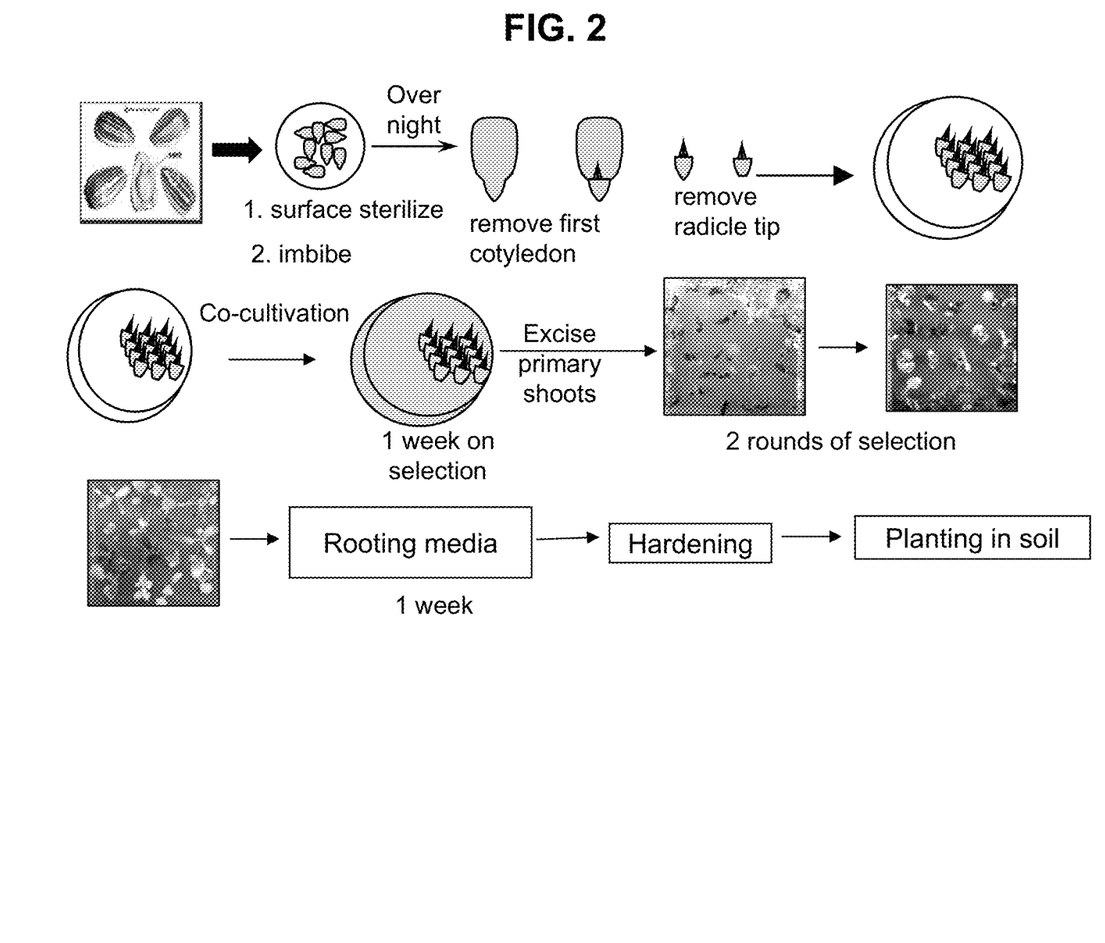
FIG. 2 shows a schematic of the various steps involved in sunflower transformation.

2. Isolated explants were cleaned by rinsing twice with sterile distilled water and were infected by adding the overnight grown re-suspended bacterial culture of 0.5 $OD_{600}$ to the explants in glass Petri plate. The culture was allowed to infect for 45 min with intermittent gentle shaking. After 45 min of infection the explants were blot dried on sterile filter paper to remove the excess liquid. Infected explants were co-cultivated by culturing on to co-cultivation medium consisting of MS basal salts (Phytotech)+MS Vitamins (Phytotech labs)+15 g/L Sucrose (Sigma)+adjust the pH to 5.8+8.5 g/L Agar+ Added Acetosyringone 200 µM while pouring to plates. The plates were incubated in dark at 25° C. for 3 days.

3. After three days co-cultivation, the elongated explants were washed twice with sterile distilled water and then with 250 mg/L carbenicillin for 10 min and again washed thrice with sterile distilled water, blot dried on sterile filter paper to remove excess liquid. Elongated root/radicle portion was cut and the shoot tip/epicotyl explants were cultured on MS-GABA-GAT medium consisting of MS basal salts (phytotech)+MS Vitamins (Phytotech labs)+30 g/L Sucrose (Sigma)+0.1 mg/L GA3+0.5 mg/L BAP adjust the pH to 5.8+8.5 g/L Agar+ 0.03 mM Glyphosate (Sigma)+250 mg/L Carbenicillin in Petriplates. The plates were incubated in light culture room (Temperature: 27±2° C.; Relative humidity: 50%; Light intensity: 40 µE m$^2$ s$^{-1}$; 16 h/8 h light/dark) for 10-12 days.

4. After 10-12 days the elongated primary shoots were excised and cultured on to MSI-GAT medium consisting of MS basal salts (phytotech)+MS Vitamins (Phytotech labs)+30 g/L Sucrose (Sigma)+0.2 mg/L IAA adjust the pH to 5.8+8.5 g/L Agar+0.03 mM Glyphosate (Sigma)+ 250 mg/L Carbenicillin in magenta flask. The magenta boxes were incubated in light culture room (Temperature: 27±2° C.; Relative humidity: 50%; Light intensity:

40 μE m$^{-2}$ s$^{-1}$ (16 h/8 h light/dark) for 8-10 days. On selection medium, the putative transgenic green shoots developed have little callus at the base. The callus portion from base was removed and the green shoots were transferred to rooting medium.

5. All the selection positive shoots (putative transgenics) that survived on MSI-GAT medium were rooted by culturing on to MSI medium (MS basal salts (phytotech)+MS Vitamins (Phytotech labs)+30 g/L Sucrose (Sigma)+0.2 mg/L IAA adjust the pH to 5.8+8.5 g/L Agar+250 mg/L Carbenicillin) and incubating for 10-12 days in light culture room (Temperature: 27±2° C.; Relative humidity: 50%; Light intensity: 40 μE m$^{2}$ s$^{-1}$ (16 h/8 h light/dark)).

Example 4

Rooting of Putative Transformed Shoots

Various hormonal combinations were tried for rooting keeping the basal medium constant. The selection positive putative shoots were cultured on to medium with different hormonal combinations as listed in Table 1 for rooting. The results of the rooting experiments were presented in Table 1.

TABLE 1

Effect of Different Rooting Medium on Direct Rooting of Putative Transformed Shoots

| Treatment* | No. of shoots | No. of shoots rooted | % Rooting | % Callusing/Vitrification |
|---|---|---|---|---|
| M1 + 1 μM AgNO3 + 1 mg L-1 IBA | 4 | 2 | 50.0 | 50.0 |
| M1 + 1 μM AgNO3 + 2 mg L-1 IBA | 6 | 4 | 66.7 | 33.3 |
| M1 + 1 μM AgNO3 + 3 mg L-1 IBA | 6 | 0 | 0.0 | 0.0 |
| M2 + 0.2 mg/L IAA | 13 | 13 | 100.0 | 0.0 |
| M2 + 0.3 mg/L IAA | 11 | 1 | 9.1 | 90.9 |
| M2 + 0.5 mg/L IAA | 4 | 0 | 0.0 | 100.0 |

*M1 = ½MS (½Macro salts + ½Vitamins + ½Sucrose) pH 5.8, Agar-8 g;
M2 (MSI) = MS (Macro salts + Vitamins + 30 g/L Sucrose) pH 5.8, Agar-8 g Effect of MSI Medium on Rooting of Putative Transformed Shoots MSI medium (MS (Macro salts+Vitamins+0.2 mg/L IAA+30 g/L Sucrose+pH 5.8, Agar-8 g) which gave best rooting and least vitrification (Table 1) was used subsequently for rooting of the putative transformed shoots (Table 2).

TABLE 2

Effect of MSI Medium on Direct Rooting of Putative Transformed Shoots of Sunflower

| Exp. No. | | Total No. of Shoots | No. of Shoots Rooted | % Rooting |
|---|---|---|---|---|
| 1 | Control | 6 | 6 | 100 |
| | Putative transformed shoots | 10 | 10 | 100 |
| 2 | Control | 9 | 9 | 100 |
| | Putative transformed shoots | 13 | 13 | 100 |
| 3 | Control | 7 | 7 | 100 |
| | Putative transformed shoots | 15 | 15 | 100 |
| 4 | Control | 7 | 7 | 100 |
| | Putative transformed shoots | 22 | 22 | 100 |
| 5 | Control | 7 | 7 | 100 |
| | Putative transformed shoots | 20 | 20 | 100 |

Example 5

Effect of Culture Conditions on Vitrification in Sunflower Inbred Line RXT004LG

Two different cultures conditions listed below (culture condition I & culture condition II) were used to study the effect of light intensity on vitrification. The results are presented below. Of the two different conditions, no vitrification was observed with culture condition I, whereas 92% vitrification was observed with culture condition II at the end of 5$^{th}$ subculture (Table 3). Subculturing is the process of transferring the explants/shoots to a fresh medium after a week's incubation in a particular medium. Four more sunflower genotypes were studied by culturing under two conditions as above, most of the lines showed less or no vitrification under culture condition I at the end of first subculture (Table 4).

TABLE 3

Effect of Culture Conditions on Vitrification in Sunflower Inbred Line RXT004LG

| Expt. No | Subculture 1** | Subculture 2** | Subculture 3** | Subculture 4** | Subculture 5** |
|---|---|---|---|---|---|
| Culture conditions-I: Temperature: 27 ± 2° C.; RH: 50%; Light: 2000-4000 lux/10-60 μE m$^{-2}$ s$^{-1}$ | | | | | |
| 1 | 0.0 | 0.0 | 0.0 | 0.0 | 0.0 |
| 2 | 0.0 | 0.0 | 0.0 | 0.0 | 0.0 |
| 3 | 0.0 | 0.0 | 0.0 | 0.0 | 0.0 |
| 4 | 0.0 | 0.0 | 0.0 | 0.0 | 0.0 |
| Average | 0.0 | 0.0 | 0.0 | 0.0 | 0.0 |
| Culture conditions-II: Temperature: 27 ± 2° C.; RH: 50%; Light: 7000-11000 Lux/100-200 μE m$^{-2}$ s$^{-1}$ | | | | | |
| 1 | 26.50 | 42.09 | 61.34 | 100.00 | 100.00 |
| 2 | 50.00 | 80.00 | 46.70 | 98.50 | 100.00 |
| 3 | 15.60 | 58.90 | 56.17 | 68.00 | 68.00 |
| 4 | 38.90 | 48.50 | 46.15 | 100.00 | 100.00 |
| Average | 32.75 | 57.37 | 52.59 | 91.63 | 92.00 |

**Data is vitrification (%) = No of shoots vitrified/total no. of shoots cultured * 100

TABLE 4

Effect of Culture Conditions on Vitrification in Different Sunflower Genotypes

| Genotype | Culture Conditions | No. of Shoots | No. of Shoots Vitrified | % Vitrification** |
|---|---|---|---|---|
| TGU002LG | Culture conditions I | 29 | 0 | 0.0 |
| | Culture conditions II | 30 | 1 | 3.3 |
| RAK001LM | Culture conditions I | 27 | 0 | 0.0 |
| | Culture conditions II | 30 | 3 | 10.0 |

TABLE 4-continued

Effect of Culture Conditions on Vitrification in Different Sunflower Genotypes

| Genotype | Culture Conditions | No. of Shoots | No. of Shoots Vitrified | % Vitrification** |
|---|---|---|---|---|
| VK106G | Culture conditions I | 30 | 17 | 56.7 |
| | Culture conditions II | 30 | 30 | 100.0 |
| A0236LG | Culture conditions I | 30 | 0 | 0.0 |
| | Culture conditions II | 30 | 19 | 63.3 |

**Data is vitrification (%) = No of shoots vitrified/total no. of shoots cultured * 100

Example 6

PCR Analysis of Transformed and Rooted Shoots to Confirm the Presence of Transgene Putative transformants that rooted were transferred to soil and were screened for presence of the gene by PCR analysis by following the standard protocol using two different sets of primers listed below. The data on PCR analysis is shown in Table 5.

Primer set 1:    Forward (SEQ ID NO: 2):
                 TTCAGCTCCACCGTATATTT

Reverse (SEQ ID NO: 3):
                 GAATCTCTTCAGCGTGTTTC

Primer set 2:    Forward (SEQ ID NO: 4):
                 CGTGTAAACAACGCTCAATA

Reverse (SEQ ID NO: 5):
                 CACAACTTTGATGCCCACAT

TABLE 5

PCR Analysis of Putative Transformants

| Exp. No. | Total No. of Explants | Explants Lost* | Net No. Explants Co-Cultivated | Total No. Plants to GH | No. of Plants Survived | No. of PCR Positive Plants | % Efficiency |
|---|---|---|---|---|---|---|---|
| 1 | 900 | 382 | 518 | 13 | 7 | 2 | 0.39 |
| 2 | 340 | 0 | 340 | 15 | 6 | 1 | 0.29 |
| 3 | 820 | 168 | 652 | 22 | 12 | 7 | 1.07 |
| 4 | 405 | 165 | 240 | 30 | 12 | 10 | 4.17 |
| 5 | 440 | 70 | 370 | 9 | 3 | 2 | 0.54 |
| 6 | 410 | 135 | 275 | 2 | 2 | 1 | 0.36 |
| 7 | 640 | 0 | 640 | 14 | 14 | 3 | 0.47 |
| 8 | 210 | 0 | 210 | 20 | 20 | 8 | 3.81 |
| | | | | | | AVE | 1.39 |

*Explants lost due to contamination/vitrification.

The T1 seeds from the T0 PCR positive plants can be collected and used for further characterization of T1 generation.

We claim:

1. A method for producing a transformed sunflower plant, the method comprising:
   a. obtaining a radicle-free mature embryonic axis explant from a non-germinated mature sunflower seed;
   b. transforming the radicle-free mature embryonic axis explant of (a) with *Agrobacterium*, wherein the *Agrobacterium* contains at least one recombinant construct comprising at least one heterologous nucleic acid of interest and a marker gene conferring resistance to a selection agent;
   c. regenerating a primary shoot from the transformed explant of (b) by culturing the explant on a first media comprising the selection agent, GA3 and BAP under cycles of a first light period followed by a first dark period wherein the first light period has a first light intensity in the range of 10-60 μE $m^{-2}$ $s^{-1}$;
   d. transferring the primary shoot of (c) to a second media comprising the selection agent and IAA;
   e. inducing rooting by culturing the primary shoot of (d) in a rooting media wherein the rooting media comprises an auxin selected from the group consisting of IAA and IBA, wherein the culturing is performed under cycles of a second light period followed by a second dark period and further wherein the second light period has a second light intensity in the range of 10-60 μE $m^{-2}$ $s^{-1}$; and
   f. producing a transformed sunflower plant from the rooted shoot of (e) wherein the transformed sunflower plant comprises in its genome at least one heterologous nucleic acid of interest.

2. The method of claim 1, wherein the *Agrobacterium* is *Agrobacterium tumefaciens*.

3. The method of claim 1 or 2, wherein the method does not involve formation of somatic embryos.

4. The method of claim 1 or 2, wherein the first light period has a first light intensity in the range of 10-50 μE $m^{-2}$ $s^{-1}$.

5. The method of claim 1 or 2, wherein the second light period has a second light intensity in the range of 10-50 μE $m^{-2}$ $s^{-1}$.

6. The method of claim 1 or 2, wherein the first light period has a first light intensity in the range of 10-50 μE $m^{-2}$ $s^{-1}$ and the second light period has a second light intensity in the range of 10-50 μE $m^{-2}$ $s^{-1}$.

7. The method of claim 1 or 2, wherein the auxin in the rooting media is IAA.

8. The method of claim 7 wherein the concentration of IAA is in the range of 0.1-1.0 mg/l.

* * * * *